(12) United States Patent
Nilsen et al.

(10) Patent No.: US 7,888,011 B2
(45) Date of Patent: Feb. 15, 2011

(54) METHODS FOR ISOLATION OF NUCLEIC ACIDS FROM PROKARYOTIC SPORES

(75) Inventors: Trine Nilsen, Arlington, MA (US); Nuno Goncalves, Somerville, MA (US)

(73) Assignee: U.S. Genomics, Inc., Woburn, MA (US)

( * ) Notice: Subject to any disclaimer, the term of this patent is extended or adjusted under 35 U.S.C. 154(b) by 465 days.

(21) Appl. No.: 11/253,051

(22) Filed: Oct. 18, 2005

(65) Prior Publication Data

US 2006/0204978 A1   Sep. 14, 2006

Related U.S. Application Data

(60) Provisional application No. 60/619,807, filed on Oct. 18, 2004.

(51) Int. Cl.
| C12Q 1/68 | (2006.01) |
| G01N 33/554 | (2006.01) |
| G01N 33/569 | (2006.01) |
| C12P 19/34 | (2006.01) |
| C12N 3/00 | (2006.01) |

(52) U.S. Cl. .................. 435/6; 435/7.32; 435/91.1; 435/242

(58) Field of Classification Search .............. 435/6, 435/91.1, 183, 7.32, 242; 436/94, 501; 536/23.1, 536/24.3, 25.3
See application file for complete search history.

(56) References Cited

U.S. PATENT DOCUMENTS

| 4,735,901 | A |   | 4/1988 | Kurtz et al. |
| 5,610,076 | A | * | 3/1997 | Founds et al. ............... 436/518 |
| 5,766,914 | A | * | 6/1998 | Deits ......................... 435/207 |
| 5,834,280 | A | * | 11/1998 | Oxenboll et al. ............ 435/190 |
| 5,922,536 | A |   | 7/1999 | Nivens et al. |
| 6,110,674 | A |   | 8/2000 | Nivens et al. |
| 6,184,020 | B1 | * | 2/2001 | Blinkovsky et al. ......... 435/212 |
| 6,210,896 | B1 |   | 4/2001 | Chan |
| 6,263,286 | B1 |   | 7/2001 | Gilmanshin et al. |
| 6,355,420 | B1 |   | 3/2002 | Chan |
| 6,403,311 | B1 |   | 6/2002 | Chan |
| 6,498,041 | B1 |   | 12/2002 | Tabacco et al. |
| 6,696,022 | B1 |   | 2/2004 | Chan et al. |
| 6,762,059 | B2 |   | 7/2004 | Chan et al. |
| 6,772,070 | B2 |   | 8/2004 | Gilmanshin et al. |
| 6,790,671 | B1 |   | 9/2004 | Austin et al. |
| 6,852,495 | B2 |   | 2/2005 | Kojima |
| 6,927,065 | B2 |   | 8/2005 | Chan et al. |
| 6,979,449 | B1 | * | 12/2005 | Mock ....................... 424/246.1 |
| 7,070,773 | B2 |   | 7/2006 | Conerly |
| 7,097,997 | B1 | * | 8/2006 | Deslys et al. ................ 435/23 |
| 7,108,974 | B2 |   | 9/2006 | Ecker et al. |
| 2002/0110818 | A1 |   | 8/2002 | Chan |
| 2002/0119455 | A1 |   | 8/2002 | Chan |
| 2002/0187508 | A1 |   | 12/2002 | Wong |
| 2002/0197639 | A1 |   | 12/2002 | Shia et al. |
| 2003/0059822 | A1 |   | 3/2003 | Chan et al. |
| 2003/0215864 | A1 |   | 11/2003 | Gilmanshin et al. |
| 2003/0235854 | A1 |   | 12/2003 | Chan |
| 2004/0009612 | A1 |   | 1/2004 | Zhao et al. |
| 2004/0053399 | A1 |   | 3/2004 | Gilmanshin |
| 2004/0166025 | A1 |   | 8/2004 | Chan et al. |
| 2004/0180328 | A1 |   | 9/2004 | Ecker et al. |
| 2004/0214211 | A1 |   | 10/2004 | Gilmanshin et al. |
| 2004/0235014 | A1 |   | 11/2004 | Nadel et al. |
| 2005/0042665 | A1 |   | 2/2005 | Gilmanshin |
| 2005/0112595 | A1 |   | 5/2005 | Zhao et al. |
| 2005/0112606 | A1 |   | 5/2005 | Fuchs et al. |
| 2005/0112620 | A1 |   | 5/2005 | Chan |
| 2005/0112671 | A1 |   | 5/2005 | Maletta et al. |
| 2005/0123944 | A1 |   | 6/2005 | Neely et al. |
| 2005/0123974 | A1 |   | 6/2005 | Gilmanshin et al. |
| 2005/0142595 | A1 |   | 6/2005 | Maletta et al. |
| 2005/0153354 | A1 |   | 7/2005 | Gilmanshin |
| 2005/0196790 | A1 |   | 9/2005 | Rooke et al. |
| 2005/0221408 | A1 |   | 10/2005 | Nalefski et al. |
| 2005/0221418 | A1 |   | 10/2005 | Fell et al. |
| 2005/0282202 | A1 |   | 12/2005 | Brolaski et al. |
| 2006/0259249 | A1 |   | 11/2006 | Sampath et al. |
| 2006/0281103 | A1 |   | 12/2006 | Burns et al. |
| 2007/0037181 | A1 |   | 2/2007 | Melkonyan et al. |
| 2007/0048735 | A1 |   | 3/2007 | Ecker et al. |

FOREIGN PATENT DOCUMENTS

| WO | WO 98/35012 A2 | 8/1998 |
| WO | WO 00/09757 A1 | 2/2000 |

OTHER PUBLICATIONS

Fairhead et al., Prevention of DNA damage in spores and in vitro by small, acid-soluble proteins from *Bacillus* species. Journal of Bacteriology, 175, 1367-1374, 1993.*

(Continued)

*Primary Examiner*—Frank W Lu
(74) *Attorney, Agent, or Firm*—Wolf, Greenfield & Sacks, P.C.

(57) ABSTRACT

The invention provides methods and related products for extracting nucleic acids such as DNA from prokaryotic spores. The invention also encompasses methods for identifying the source of such spores via analysis of the isolated nucleic acids.

12 Claims, 2 Drawing Sheets

OTHER PUBLICATIONS

Kuske et al., Small-Scale DNA Sample Preparation Method for Field PCR Detection of Microbial Cells and Spores in Soil. Applied and Environmental Microbiology, 64, 2463-2472, 1998.*

Macdonald et al., Comparison of Pulsed-Field Gel Electrophoresis DNA Fingerprints of Field Isolates of the Entomopathogen *Bacillus popilliae*. Applied and Environmental Microbiology, 61, 2446-2449, 1995.*

The definition of "prokaryote" from Wikipedia, the free encyclopedia. Printed on Dec. 18, 2009.*

The definition of "archaea" from Wikipedia, the free encyclopedia. Printed on Dec. 18, 2009.*

Atrih et al., Structural analysis of *Bacillus subtilis* 168 endospore peptidoglycan and its role during differentiation. J Bacteriol. Nov. 1996;178(21):6173-83.

Cano et al., Revival and identification of bacterial spores in 25- to 40-million-year-old Dominican amber. Science. May 19, 1995;268(5213):1060-4. Abstract Only.

Driks et al., Morphogenesis and properties of the bacterial spore. In Prokaryotic development, ASM Press, 2000. p. 191-218.

Fairhead et al., Binding of DNA to alpha/beta-type small, acid-soluble proteins from spores of *Bacillus* or *Clostridium* species prevents formation of cytosine dimers, cytosine-thymine dimers, and bipyrimidine photoadducts after UV irradiation. J Bacteriol. May 1992;174(9):2874-80.

Goldman et al., *Bacillus subtilis* spore coats: complexity and purification of a unique polypeptide component. J Bacteriol. Sep. 1978;135(3):1091-106.

Griffith et al., Electron microscopic studies of the interaction between a *Bacillus subtilis* alpha/beta-type small, acid-soluble spore protein with DNA: protein binding is cooperative, stiffens the DNA, and induces negative supercoiling. Proc Natl Acad Sci U S A. Aug. 16, 1994;91(17):8224-8.

Ivnitski et al., Nucleic acid approaches for detection and identification of biological warfare and infectious disease agents. Biotechniques. Oct. 2003;35(4):862-9. Abstract Only.

Jenkinson et al., Synthesis and order of assembly of spore coat proteins in *Bacillus subtilis*. J Gen Microbiol. 1981;123:1-16.

Kornberg et al., Origin of proteins in sporulation. Annu Rev Biochem. 1968;37:51-78.

La Duc et al., *Bacillus odysseyi* sp. nov., a round-spore-forming *Bacillus* isolated from the Mars Odyssey spacecraft. Int J Syst Evol Microbiol. Jan. 2004;54(Pt 1):195-201.

Mohr et al., Binding of small acid-soluble spore proteins from *Bacillus subtilis* changes the conformation of DNA from B to A. Proc Natl Acad Sci U S A. Jan. 1, 1991;88(1):77-81.

Nicholson et al., Dramatic increase in negative superhelicity of plasmid DNA in the forespore compartment of sporulating cells of *Bacillus subtilis*. J Bacteriol. Jan. 1990;172(1):7-14.

Nicholson et al., Binding of DNA in vitro by a small, acid-soluble spore protein from *Bacillus subtilis* and the effect of this binding on DNA topology. J Bacteriol. Dec. 1990;172(12):6900-6.

Pandey et al., Properties of the *Bacillus subtilis* spore coat. J Bacteriol. Mar. 1979;137(3):1208-18.

Pogliano et al., Visualization of the subcellular location of sporulation proteins in *Bacillus subtilis* using immunofluorescence microscopy. Mol Microbiol. Nov. 1995;18(3):459-70.

Popham et al., Analysis of the peptidoglycan structure of *Bacillus subtilis* endospores. J Bacteriol. Nov. 1996;178(22):6451-8.

Santo et al., Ultrastructural analysis during germination and outgrowth of *Bacillus subtilis* spores. J Bacteriol. Oct. 1974;120(1):475-81.

Setlow et al., DNA in dormant spores of *Bacillus* species is in an A-like conformation. Mol Microbiol. Mar. 1992;6(5):563-7. Abstract Only.

Warth et al., Structure of the peptidoglycan from spores of *Bacillus subtilis*. Biochemistry. Apr. 11, 1972;11(8):1389-96.

Warth et al., Structure of the peptidoglycan from vegetative cell walls of *Bacillus subtilis*. Biochemistry. Nov. 23, 1971;10(24):4349-58.

Warth et al., Structure of the peptidoglycan of bacterial spores: occurrence of the lactam of muramic acid. Proc Natl Acad Sci U S A. Oct. 1969;64(2):528-35.

Kutchma et al., Small-scale isolation of genomic DNA from *Streptomyces* mycelia or spores. Biotechniques. Mar. 1998;24(3):452-6.

Berendzen et al., A rapid and versatile combined DNA/RNA extraction protocol and its application to the analysis of a novel DNA marker set polymorphic between *Arabidopsis thaliana* ecotypes Col-0 and Landsberg erecta. Plant Methods Aug. 23, 2005;1(1):4, pp. 1-15.

Cummings et al., A simple and efficient method for isolating genomic DNA from endomycorrhizal spores. Gene Anal Tech. Sep.-Oct. 1989;6(5):89-92.

Farrell et al., *Bacillus globigii* bugbeads: a model simulant of a bacterial spore. Anal Chem. Jan. 15, 2005;77(2):549-55.

Paidhungat et al., Genetic requirements for induction of germination of spores of *Bacillus subtilis* by Ca(2+)-dipicolinate. J Bacteriol. Aug. 2001;183(16):4886-93.

Paidhungat et al., Role of ger proteins in nutrient and nonnutrient triggering of spore germination in *Bacillus subtilis*. J Bacteriol. May 2000;182(9):2513-9.

Ragkousi et al., Transglutaminase-mediated cross-linking of GerQ in the coats of *Bacillus subtilis* spores. J Bacteriol. Sep. 2004;186(17):5567-75.

Riesenman et al., Role of the spore coat layers in *Bacillus subtilis* spore resistance to hydrogen peroxide, artificial UV-C, UV-B, and solar UV radiation. Appl Environ Microbiol. Feb. 2000;66(2):620-6.

Van Doorn et al., Silica-guanidinium thiocyanate-based nucleic acid isolation protocol does not improve sensitivity of two commercial tests for detection of *Mycobacterium tuberculosis* in respiratory samples. Eur J Clin Microbiol Infect Dis. Oct. 2006;25(10):673-5.

Vary, Germination of *Bacillus megaterium* spores after various extraction procedures J Bacteriol. Nov. 1973;116(2):797-802.

* cited by examiner

METHODS FOR ISOLATION OF NUCLEIC ACIDS FROM PROKARYOTIC SPORES

RELATED APPLICATIONS

This application claims priority to U.S. provisional application having Ser. No. 60/619,807, entitled "METHODS FOR REMOVAL OF NUCLEIC ACIDS FROM PROKARYOTIC SPORES", filed on Oct. 18, 2004, the entire contents of which are incorporated by reference herein.

GOVERNMENT SUPPORT

This invention was made in part with government support under Contract No. W81XWH-04-9-0011 from the Homeland Security Advanced Research Projects Agency. The Government may retain certain rights in the invention.

FIELD OF THE INVENTION

Methods of extracting and isolating nucleic acids, particularly high molecular weight nucleic acids, from prokaryotic spores are provided by the invention.

BACKGROUND OF THE INVENTION

Certain species of bacteria are unique in their ability to form metabolically dormant spores. Spore formation is usually the result of a response to nutrient exhaustion in the surrounding habitat of the cell and serves to protect the organism from harsh environments such as extreme heat, dehydration, UV and gamma-radiation and mechanical stress until conditions once again become suitable for metabolic activity to resume (Driks and Setlow, 2000). The most effective spore-formers are species of *Bacillus* and *Clostridium* which have been shown to remain dormant for millions of years as well as survive the harsh environments of outer space (Cano and Borucki, 1995; La Duc et al., 2004). Recently, certain spore-forming bacteria such as certain *Bacillus* species have been used as biowarfare agents (e.g., weaponized *B. anthracis* spores).

The morphology of a prokaryotic spore varies between species but for the most part consists of a condensed core, an inner spore membrane, a cortex, an inner and an outer spore coat and, in some cases, an exosporium (Santo and Doi, 1974). The spore coat is the outermost structure. It is common to all spores and is largely made up of protein (Kornberg et al., 1968). The composition of each layer is different and unique between spore types. For example, spores differ in the number and types of proteins in their coats, as well as the structure and modification of such proteins. The coat of *B. cereus* consists of one predominant coat protein present in a single layer, while the coat of *B. subtilis* contains upwards of 20 different proteins that contribute to two distinct coat layers (Aronson and Horn, 1976; Goldman and Tipper 1978, Pandey and Aronson, 1978; Jenkinson et al., 1981).

The spore cell wall is largely comprised of a thick cortex, consisting of two distinct types of peptidoglycan (Warth and Strominger, 1969, 1971, 1972). The germ cell wall is the layer closest to the inner forespore membrane. It has the same chemical composition as the mother cell and is believed to function as a template for peptidoglycan synthesis during spore germination. There is significant structural variation between species in the germ cell wall peptidoglycan. The structure of the cortex peptidoglycan, on the other hand, is similar in all species that have been examined to date, but it is slightly different from that of the mother cell. It has about 50% of its N-acetyl muramic acid residues substituted with muramic acid-delta-lactam, and has 10-12 fold less cross-linking between the glycan strands (Arith et al., 1996; Popham et al., 1996).

DNA exists within the spore core in a highly dehydrated state. Just prior to completion of spore maturation, the cell produces an over-abundance of small acid-soluble proteins (SASPs) (Nicholson and Setlow, 1990; Pogliano et al., 1995). The SASPs bind non-specifically to the DNA and, in dehydrated conditions, convert the DNA structure from its native B-form to an A-form (Griffith et al., 1994; Mohr et al., 1991; Setlow, 1992, Nicholson et al., 1990). It is this conformational change to DNA that has been shown to give the spore increased resistance to UV radiation (Fairhead and Setlow, 1992; Mohr et. al., 1991).

Isolation of DNA from prokaryotic spores would enable identification and analysis of such spores. Since spores are characteristically known for their resilience to chemical, enzymatic and mechanical damage, the methods previously used to lyse spores employed extreme and harsh measures that released DNA but also exposed it to harsh environments that compromised its structural integrity. The degree of damage to the isolated DNA was primarily dependent on the technique used to break open the spore and extract the genomic DNA. Because the spore is naturally highly resistant to enzymatic and chemical treatments, many methods have resorted to mechanical means for opening the spores and releasing the DNA. These techniques included boiling, French press, glass bead grinding, freeze/thaw cycles, and sonication (Taylor et al., 2001). Furthermore, mechanical disruption of spores to extract DNA was often preferred in order to avoid using chemicals and enzymes that would inhibit downstream PCR steps (Ivintski et al., 2003). These stresses however have a direct impact on the spore DNA once it is released and exposed to the same turbulent environment used to break open the spores. Even techniques used to purify DNA from the mixture of digested spore components (as well as from the large excesses of SASPs that coat DNA) can shear DNA. These steps include affinity chromatography columns, phenol/chloroform extraction, DNA precipitation by alcohols, vortexing and high speed centrifugation.

Accordingly, traditional methods of genomic DNA isolation from mature, non-germinating spores typically yielded fragments of DNA that averaged a few kilobases (kb) in length. DNA of this size is suitable for applications that rely on amplification of a specific section of DNA that is then used for DNA cloning, genetic analysis, etc. (Ivnitski, et. al., 2003). For manipulations involving polymerase chain reaction (PCR), the state and size of the harvested DNA was usually sufficient. However, for more detailed analysis on genome organization and/or phylogenic studies, the DNA isolated using these methods was insufficient.

There is a need for methods that rapidly and reliably yield high molecular weight nucleic acids from prokaryotic spores since such nucleic acids would facilitate analysis and identification of spores.

SUMMARY OF THE INVENTION

The invention is premised in part on the discovery of methods for extracting high molecular weight (HMW) nucleic acids from prokaryotic spores. These nucleic acids include genomic DNA. The ability to extract (i.e., harvest) and preferably isolate such nucleic acids from prokaryotic spores facilitates detection of biohazardous spores such as weaponized *B. anthracis* and thereby minimizes potential infection and spread throughout a population.

The invention provides a non-mechanical method for extracting HMW nucleic acids from prokaryotic spores. The method does not rely on germination of spores and, accordingly, non-germinated spores can be used as the starting source. The method also does not rely on an amplification step such as an in vitro amplification step. As a result, the HMW nucleic acids are referred to herein as non in vitro amplified nucleic acids. The extraction method is rapid; it can be performed in a less than 2 hours. This greatly expedites the determination of whether a suspect sample contains the biohazardous spore, thereby expediting implementation of containment measures and treatment.

Thus, the invention provides methods for harvesting (i.e., extracting) nucleic acids from prokaryotic spores, and compositions comprising and methods of analyzing nucleic acids harvested according to such methods.

In one aspect, the invention provides a method for harvesting nucleic acids from prokaryotic spores comprising contacting prokaryotic spores with a decoating solution for a time and under conditions sufficient to degrade a spore coat and produce decoated spores, and sequentially contacting decoated spores with a first and a second lysing solution for times and under conditions sufficient to degrade a spore cell wall and proteins. If desired, the method may also comprise a step of fractionating high molecular weight nucleic acids based on size.

In one embodiment, the prokaryotic spores are bacterial spores, such as but not limited to gram positive bacterial spores. The bacterial spores may be *Bacillus* spores, such as but not limited to *B. anthracis* spores. The bacterial spores may be *Clostridium* spores. The prokaryotic spores may be non-germinating.

In one embodiment, the method is a non-mechanical method of harvesting nucleic acids. That is, it does not require excessive agitation and shearing forces which may be encountered in vortexing, and other mechanical stresses as described herein.

In one embodiment, the decoating solution comprises a denaturant such as but not limited to urea. In one embodiment, the decoating solution comprises a detergent such as but not limited to SDS. In one embodiment, the decoating solution comprises a reducing agent such as but not limited to β-mercaptoethanol. In one embodiment, the decoating solution comprises a chelator such as but not limited to EDTA. In one embodiment, the decoating solution comprises a buffer such as but not limited to Tris.

In one embodiment, the time sufficient to degrade the spore coat is less than 60 minutes, less than 45 minutes, less than 30 minutes, less than 15 minutes, less than 10 minutes, about 5 minutes, or less.

In one embodiment, the conditions sufficient to degrade the spore coat include high temperature. High temperature may be greater than 75° C., greater than 80° C., greater than 85° C., about 90° C., or about 95° C., or more. Preferably it is about 90° C. Conditions sufficient to degrade the spore also include the pH of the decoating solution. The pH may be greater than 8, about 8.5, about 9, about 9.5, about 10, about 10.5, or about 11. In one embodiment, the decoating solution is about pH 10.

In one embodiment, the decoated spores are contacted with a washing solution prior to contact with the first lysing agent. The decoated spores may be washed once, twice, thrice or more times. Preferably, they are washed more than once. In one embodiment, the washing solution is mildly basic and comprises detergents. A mildly basic solution is one having a pH above 7, above 7.5, above 8, above 8.5, or about 9. In one embodiment, the washing solution has a pH of about 8. In one embodiment, the detergents are Triton-X-100 and Tween-20.

In one embodiment, the washing solution comprises a buffering agent and a chelator. In related embodiments, the buffering agent is Tris and/or the chelator is EDTA.

In one embodiment, the first lysis solution comprises detergents and is mildly basic. In related embodiments, the detergents are Triton-X-100 and Tween-20 and/or the first lysis solution has a pH of about 8. In one embodiment, the first lysis solution comprises a hydrolyzing (or hydrolytic) enzyme such as but not limited to lysozyme. In one embodiment, the spores are incubated with the first lysis solution for about one hour at 37° C. The time of incubation can vary and may be for example less than 3 hours, less than 2 hours, or less than 1 hour. The temperature can also vary and may be for example at least 25° C., at least 30° C., at least 35° C., less than 40° C., less than 42° C., less than 45° C., less than 50° C., or less than 55° C.

In one embodiment, the second lysis solution comprises a protease such as but not limited to proteinase K. In one embodiment, the second lysis solution comprises a denaturant such as but not limited to urea. In one embodiment, the second lysis solution comprises a mild detergent such as but not limited N-lauryl sarcosine. In one embodiment, the second lysis solution comprises a reducing agent such as but not limited to β-mercaptoethanol. In one embodiment, the second lysis solution comprises a buffering agent and a chelator. In related embodiments, the buffering agent is Tris and/or the chelator is EDTA. In one embodiment, the second lysis solution is about neutral pH. Neutral pH includes a pH in the range of about 6.5 to about 7.5. Preferably it is about 7 or about 7.4.

In one embodiment, the nucleic acids are isolated. In another embodiment, the nucleic acids are high molecular weight nucleic acids. In other embodiments, the nucleic acids are not high molecular weigh nucleic acids, and they are optionally not isolated from other components of the second lysis mixture.

In one embodiment, if the nucleic acids are fractionated, they are fractionated by dialysis. In another embodiment, the nucleic acids are fractionated by field flow fractionation. High molecular weight nucleic acids can be fractionated and/or isolated accordingly.

In one embodiment, the nucleic acid is a high molecular weight nucleic acid (i.e., it is at least 30 kilobases in size). In another embodiment, the high molecular weight nucleic acid is at least 100 kilobases in size.

In one embodiment, at least 90% of prokaryotic spores are lysed.

In another aspect, the invention provides a method for harvesting high molecular weight nucleic acids from a prokaryotic spore comprising degrading a prokaryotic spore coat using a denaturant and a detergent in a basic solution (for example in a decoating solution), lysing a prokaryotic spore cell wall using a hydrolytic enzyme such as but not limited to lysozyme (for example in a first lysis solution), degrading proteins using a protease, a denaturant, and a mild detergent (for example in a second lysis solution), and optionally fractionating high molecular weight nucleic acids based on size. The various embodiments recited above apply equally to this aspect of the invention.

In another aspect, the invention provides a composition comprising an isolated non in vitro amplified high molecular weight nucleic acid harvested from a prokaryotic spore. The various embodiments recited above apply equally to this aspect of the invention.

In yet another aspect, the invention provides a method for detecting a prokaryotic spore in a sample comprising harvesting high molecular weight nucleic acid from a sample according to the methods described herein, and identifying a high molecular weight nucleic acid that is indicative of a prokaryotic species. The various embodiments recited above apply equally to this aspect of the invention.

These and other aspects of the invention, as well as various advantages and utilities, will be more apparent with reference to the detailed description of the preferred embodiments and to the accompanying figures.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the figures. The invention is capable of other embodiments and of being practiced or of being carried out in various ways.

The phraseology and terminology used herein is for the purpose of description and should not be regarded as limiting. The use herein of "including", "comprising", "having", "containing", "involving", and variations thereof, is meant to encompass the items listed thereafter and equivalents thereof as well as additional items.

BRIEF DESCRIPTION OF THE FIGURES

It is to be understood that the Figures are not required for enablement of the invention.

DETAILED DESCRIPTION OF THE INVENTION

The invention relates in part to extraction of nucleic acids from prokaryotic spores. More specifically, the invention provides methods for rapidly extracting nucleic acids from prokaryotic spores. The nucleic acids in some embodiments are high molecular weight (HMW) nucleic acids. Such HMW nucleic acids include genomic DNA. The methods of the invention yield HMW nucleic acids from fully-matured spores of prokaryotic organisms with high efficiency.

The ability to extract (i.e., harvest) and/or isolate HMW nucleic acids, optionally in high yields, from prokaryotic spores is useful for many purposes, including the ability to identify the source of the nucleic acid and thus the nature of the spores. It also facilitates manipulation of such nucleic acids in vitro. This could be useful in creating an attenuated strain of the prokaryote.

The invention provides a novel means of extracting nucleic acids from spores. This method employs a chemical spore de-coating step, followed by a chemical and enzymatic lytic step that degrades the cortex and denatures and enzymatically digests proteins without significantly affecting the exposed DNA. The resultant mixture is a viscous solution of HMW nucleic acid, digested proteins, peptidoglycan fragments, and other small molecules released from the cytoplasm and cell walls (e.g., lipids, carbohydrates, nucleotides etc.).

The extraction method of the invention therefore is a non-mechanical extraction method. Various steps rely on chemical and/or enzymatic disruption of spore components. The method does not rely on mechanical stresses to disrupt the spore however since this tends to shear the nucleic acids. Agitation, if used at all, is gentle agitation. The method also does not require amplification of nucleic acids such as by polymerase chain reaction (PCR).

The method first disrupts the inner and outer coats of the spore, which consist mainly of protein. This allows access to the cortex, which is a peptidoglycan layer. The resulting de-coated spore is gently digested and opened through a series of chemical and enzymatic reactions that release the nucleic acids contained therein (such as genomic DNA) into solution with minor disruption. The resultant mixture is then fractionated to remove degraded proteins, lipids, carbohydrates and relatively small nucleic acids based primarily on size. The separation of DNA from this solution can be performed if the DNA is to be further manipulated, since contaminating material may inhibit or interfere with any of the contemplated downstream processes.

Size fractionation can be carried out via dialysis of the mixture using dialysis tubing or membranes with particularly desired cut-offs. Examples of suitable cut-offs are 100-500, 000 kDa. Dialysis membrane include PVDF membrane, regenerated cellulose and cellulose ester. Such membranes are commercially available from sources such as Spectrum Labs and Millipore.

Size fractionation can similarly be carried out via field flow fractionation (FFF). FFF is a flow-based technique which utilizes an unobstructed, thin fluid in a channel that may be only several hundred micrometers thick in order to separate molecules based on size. FFF is described in U.S. Pat. Nos. 4,147,621; 4,214,981; 4,250,026; 4,737,268; 4,830,756; 4,894,146; 5,039,426; 5,141,651; 5,156,039; and 5,193,688, among others. FFF is able to fractionate molecules, including nucleic acids, according to size, as described in U.S. patent application Ser. No. 11/180,980 filed Jul. 13, 2005. The mixture is applied to an FFF device and moved through thereby separating HMW nucleic acids from most if not all smaller components in the mixture.

A detailed protocol for isolating HMW genomic DNA from spores is provided in the Examples. This protocol yields isolated genomic DNA that has a length upwards of 2,000 kb as shown in FIG. 1A. Not I restriction enzyme digestion of DNA isolated from *B. anthracis* spores yields an expected pattern of fragments based upon genome sequence data with fragment lengths up to 641 kb (FIG. 1B and FIG. 2), and verifies that DNA isolated by this method is clean enough for further enzymatic reactions.

Briefly, the method involves the steps described herein. The spores are initially decoated using a decoating buffer or solution, followed by cell wall lysis using a first lysis buffer or solution, and protein degradation using a second lysis buffer or solution. This may optionally be followed by size fractionation, as described herein.

The decoating buffer or solution comprises a denaturant, a detergent, a reducing agent, a chelator and a buffering agent. As used herein, a denaturant is a compound that structurally alters a molecule thereby disrupting its biological activity. The terms denaturant and denaturing agent are used interchangeably herein. Examples of denaturants include urea and guanidinium hydrochloride. A preferred denaturant in the decoating solution is urea.

As used herein, a detergent is an ampiphilic compound that may be ionic, non-ionic or zwitterionic. Examples of detergents include sodium dodecylsulfate (SDS) (strong), Tween 20 (medium), octylphenolpoly(ethyleneglycolether)$_{10}$ (Triton X-100) (medium), N-lauryl sarcosine-Na$^+$ salt (Sarkosyl) (mild), n-dodecyl-N,N-dimethyl-3-ammonio-1-propanesulfonate (strong), CHAPSO (strong), CHAPS (strong), isotridecylpoly(ethyleneglycolether)8 (strong), dodecylpoly(ethyleneglycolether)$_9$ (Thesit) (strong), polyethylene glycol (PEG 2000) (medium), octylphenolpoly(ethyleneglycolether)$_7$ (Triton X-114) (medium), n-dodecyl-beta-D-maltoside (mild), decanoyl-n-methylglucamide (mild), octanoyl-N-methylglucamide (mild), n-dodecyl-glucoside (mild), and n-octyl-glucoside (mild). A preferred detergent in the decoating solution is SDS.

As used herein, a reducing agent is a compound that chemically reduces molecules, usually by donating an electron(s). Reducing agents are able to reduce the number of disulfide bridges or linkages that are formed following denaturation of proteins. The presence of a reducing agent therefore prevents a denatured protein from renaturing and potentially precipitating out of solution. Examples of reducing agents include β-mercaptoethanol (βME) and dithiothreitol (DTT). A preferred reducing agent in the decoating solution is βME.

As used herein, a chelator is a compound that ionically binds (and thus removes from solution and/or reduces the concentration of) cations. Examples include EDTA (which removes divalent cations such as Mg2+) and EGTA. A preferred chelator in the decoating solution is EDTA.

As used herein, a buffering agent is a compound that maintains the pH of a solution. Each buffering agent has a characteristic buffering range through which it performs optimally. Examples of buffering agent include Tris and phosphate buffered saline. A preferred buffering agent in the decoating solution is Tris.

The decoating solution is generally a highly basic solution. Preferably, it has a pH above 8, preferably about 8, 8.5, 9, 9.5, 10, 10.5 or 11, and more preferably at about 10. The decoating step can occur at a range of temperatures. It can be performed at higher temperatures for shorter periods of time, or lower temperatures for longer periods of time. Preferably, the step is performed at about 90° C. for 5 minutes.

Following the decoating step, the spores are washed in a washing solution that comprises one or more detergents, a chelator and a buffering agent. The detergents are generally chosen from those that are milder than SDS. Preferably, the washing solution contains Tween 20 and Triton-X-100 as detergents. The buffering agent is preferably Tris, and the chelator is preferably EDTA. The solution preferably has a mildly basic pH (e.g., pH of about 7, 7.5, 8, 8.5 or 9), and more preferably about pH 8.

The first lysis solution comprises one or more detergents, a chelator, a buffering agent, and a hydrolyzing enzyme. Preferably, the first lysis solution is a 10-fold concentrate of the washing solution with hydrolyzing enzyme added. The hydrolyzing enzyme is an enzyme that degrades the cell wall, preferably degrading beta 1,4-glycosidic bonds (and thus degrading peptidoglycans of the cell wall). In a preferred embodiment it is lysozyme. Other examples are known in the art. The lysozyme can be naturally occurring or recombinant. The first lysis step can be carried out at a broad range of temperatures, dependent mainly on the activity-temperature profile of the enzyme used. In a preferred embodiment, the step is carried out at 37° C. for 60 minutes. It is expected that temperatures in the range of 25° C. to 45° C. would be suitable however longer incubation times would likely be necessary.

The second lysis solution comprises a denaturant, a detergent, a reducing agent, a chelator, a buffering agent, and a protease. Preferably, the denaturant is urea, the detergent is a mild detergent such as N-lauryl sarcosine, the reducing agent is βME (or DTT), the chelator is EDTA, and the buffering agent is Tris. The protease may be any protease. In a preferred embodiment, it is proteinase K. The pH of the second lysis solution is more neutral than the solutions used before it. Preferably it has a pH of between about 7 and about 8, more preferably of about 7.4. The second lysis step can be carried out at a broad range of temperatures, dependent mainly on the activity-temperature profile of the protease used. In a preferred embodiment, the step is carried out at 55° C. for 30 minutes. It is expected that temperatures in the range of 25° C. to 70° C. would be suitable however longer incubation times may be necessary.

The various incubations may be carried out in water baths, incubators, temperature controlled rooms, and the like. Temperature controlled water baths are preferred.

The fractionation step if carried out using dialysis generally involves various changes of dialyzing solution. As an example, a 1:100 dilution of the first lysis solution may be replaced by a 1×TE (10 mM Tris, 1 mM EDTA, pH 8), followed by water. FFF can be carried out in a 1×TE solution also. One of ordinary skill in the art will be able to modify these solutions according to particular needs and based on the ordinary skill in the art.

In more specific embodiments, the decoating solution comprises urea, SDS, β-mercaptoethanol, Tris and EDTA, and has a pH of about 10, the first lysis solution comprises lysozyme, Tris, EDTA, Triton X 100 and Tween 20, and has a pH of about 8, and the second lysis solution comprises urea, β-mercaptoethanol (or dithiothreitol, DTT), N-lauryl sarcosine, Tris, EDTA, and a protease such as but not limited to proteinase K, and has a pH of about 7.4. In one embodiment size fractionation, if performed, can be accomplished using dialysis using PVDF membrane having a 500,000 kDa size exclusion.

The method has repeatedly demonstrated yields of about 1 μg DNA from 10$^8$ initial spores. The method also has repeatedly demonstrated a high efficiency of lysis of spores. For example, lysis of greater than 90% of initial spore numbers is routinely observed.

The methods provided herein do not require the germination of spores. It is therefore particularly useful since not all prokaryotic spores can be induced to germinate under laboratory setting. Samples can be collected and tested for the presence of spores without any need for culture or germination, leading to a more rapid and potentially more exhaustive determination of spore presence and/or identification.

The invention therefore also provides methods for identifying prokaryotes, via identification of their spores. The prokaryotes may be naturally occurring or genetically engineered "hybrid" organisms. The prokaryotic organisms include bacteria such as pathogenic bacteria. The bacteria may be gram positive bacteria. These include *Bacillus* species such as *B. anthracis* (the causative agent of anthrax), *B. cereus, B. globigii, B. subtilis, B. thuringiensis, Lactobacillus, Clostridium* species such as *C. tetani* (the causative agent of tetanus), *C. botulinum* (the causative agent of botulism), *C. novyi, C. histolyticum, C. sordellii*, and *C. difficile*, and *Sulfobacillus* species such as *S. disulfidooxidans*. Spore-forming prokaryotes also include *Mycobacteria* and *Corynebacteria*. The prokaryotes may be food pathogens, water-borne pathogens, and/or aerosolized pathogens.

The methods can be used to harvest nucleic acids from a plurality of spores. As used herein, a plurality of spores is more than one and less than an infinite number. It includes less than $10^{10}$, less than $10^9$, less than $10^8$, less than $10^7$, less than $10^6$, less than $10^5$, less than $10^4$, less than 5000, less than 1000, less than 500, less than 100, less than 50, less than 25, less than 10 and less than 5, as well as every integer therebetween as if explicitly recited herein. The plurality of spores may comprise identical spores or diverse spores. If the sample contains diverse spores, there may be two, three, four, five or more different types of spores in a given sample. The identification methods described herein are able to discern the resultant nucleic acids and attribute a prokaryotic source to each.

The method of the invention yields HMW nucleic acids. As used herein, HMW nucleic acids denote nucleic acids that are at least 30 kb in length. HMW nucleic acids can be at least 35 kb, at least 40 kb, at least 45 kb, at least 50 kb, at least 75 kb, at least 100 kb, at least 250 kb, at least 500 kb, at least 1000 kb, at least 2000 kb, or longer, as well as every integer therebetween as if explicitly recited herein. They are limited in size only by the actual length of the nucleic acid in the spore. For example, if the spore contains a single chromosome that is about 4 Mb in length, then the length of the HMW nucleic acid may be up to and including the full length of such a chromosome.

In other aspects, the methods of the invention can be used to harvest nucleic acids that are less than 30 kb in size. Such nucleic acids may still be useful for a number of applications, and the methods provided herein would still expedite the extraction and optionally isolation of such nucleic acids. Accordingly, the invention is useful for extracting nucleic acids from prokaryotic spores rapidly and efficiently.

As used herein, the term nucleic acid means multiple nucleotides (i.e., molecules comprising a sugar (e.g., ribose or deoxyribose) linked to an exchangeable organic base, which is either a substituted pyrimidine (e.g., cytosine (C), thymidine (T) or uracil (U)) or a substituted purine (e.g., adenine (A) or guanine (G)). "Nucleic acid" and "nucleic acid molecule" are used interchangeably. As used herein, the terms refer to oligoribonucleotides as well as oligodeoxyribonucleotides. The terms shall also include polynucleosides (i.e., a polynucleotide minus a phosphate) and any other organic base containing polymer. Nucleic acid such as nucleic acid probes can be obtained from existing nucleic acid sources (e.g., genomic or cDNA), or by synthetic means (e.g., produced by nucleic acid synthesis).

Nucleic acids include DNA and RNA and derivatives thereof. DNA includes genomic and plasmid DNA. RNA includes mRNA and rRNA. As used herein, a target nucleic acid is the nucleic acid being analyzed.

Preferably, prior amplification using techniques such as PCR are not necessary. Accordingly, the nucleic acid is a non in vitro amplified nucleic acid. As used herein, a "non in vitro amplified nucleic acid" refers to a nucleic acid that has not been amplified in vitro using techniques such as PCR or recombinant DNA methods. A non in vitro amplified nucleic acid may however be a nucleic acid that is amplified in vivo (in the biological sample from which it was harvested) as a natural consequence of the development of the cells in vivo. This means that the non in vitro nucleic acid may be one which is amplified in vivo as part of locus amplification.

In some embodiments, the HWM nucleic acids are isolated. As used herein, an isolated nucleic acid is a nucleic acid that is physically separated from components with which it is normally associated in nature. As an example, an isolated nucleic acid may be one which is separated from a spore, a spore coat, a cortex, proteins, polysaccharides and the like, or a combination thereof.

The nucleic acids may be double-stranded or single-stranded. Single-stranded nucleic acids can be generated by modulating the environment of a double-stranded nucleic acid including singly or in combination increasing temperature, decreasing salt concentration, and the like. Methods of denaturing nucleic acids are known in the art.

Samples to be tested for the presence of prokaryotic spores can be derived from virtually any source known or suspected to contain a spore of interest. Samples can be solid, liquid or gaseous in nature. They may be purified but usually are not.

The samples can be a biological or bodily sample such as a tissue biopsy, urine, sputum, semen, stool, saliva and the like. The invention further contemplates preparation and analysis of samples that may be biowarfare targets. Air, liquids and solids that will come into contact with a significant number of people are most likely to be biowarfare targets. Samples to be tested for the presence of such agents may be taken from an indoor or outdoor environment. Such sampling can occur continuously, although this may not be necessary in every application. For example, in an airport setting, it may only be necessary to sample near or around select baggage. In other instances, it may be necessary to continually sample the environment. These latter instances may occur in "heightened alert" states.

Air samples can be tested for the presence of normally airborne spores as well as aerosolized (or weaponized) spores. Air samples can be taken from a variety of places suspected of being biowarfare targets including public places such as airports, hotels, office buildings, government facilities, mail facilities, money handling facilities, and public transportation vehicles such as buses, trains, airplanes, and the like.

The choice of air sampling instruments is dependent on user requirements, and those of ordinary skill in the art will be able to identify the appropriate instrument for a particular application. Various air sampling devices are currently commercially available from sources such as BioAerosol Concentrator, International pbi S.pA., Meso Systems, Sceptor Industries, Inc., and Anderson. Moreover, techniques for air sampling are described in J. P. Lodge, Jr. Methods of Air Sampling and Analysis, Third Edition, Lewis Publishers, Inc. (Dec. 31, 1988) ISBN 0873711416.

Liquid samples can be taken from public water supplies, water reservoirs, lakes, rivers, wells, springs, and commercially available beverages.

Solids such as food (including baby food and formula), money (including paper and coin currencies), public transportation tokens, books, mail, and the like can also be sampled via swipe, wipe or swab testing and placing the swipe, wipe or swab in a liquid for dissolution of any spores attached thereto. Based on the size of the swipe or swab and the volume of the corresponding liquid it must be placed in for dissolution, it may or may not be necessary to concentrate such liquid sample prior to further manipulation.

Once the HMW nucleic acids are extracted and possibly isolated, the source of the nucleic acids, and thus the identity of the spores, can be accomplished using genetic analysis techniques known in the art.

One method of analysis simply requires digestion of the HMW nucleic acid with a rare cutting restriction enzyme and analysis of the fragments so generated. The source of the nucleic acid may be identified based on a single fragment of a unique size or on a pattern of fragments generated using a particular enzyme. The fragments are usually physically separated from each other using, for example, pulse field gel electrophoresis, as shown in the Examples and Figures.

Another method utilizes direct linear analysis (DLA). DLA applications have several advantages. DLA can analyze DNA of significantly greater lengths and integrity (e.g., >150 kb and free of nicks) for appropriate manipulations like restriction enzyme digestion, motif tagging and backbone staining. It does not however require amplification of specific sequences and it yields genome organization information.

Yet another method analyzes the nucleic acid based on the binding patterns of probes. Such probes preferably bind to nucleic acids in a sequence-specific or structure-specific manner, and include but are not limited to nucleic acid probes and cleaving and non-cleaving enzymes but are not so limited. The sequence or structure recognized and bound by the probe may be unique to that nucleic acid. Alternatively, the sequence itself is not unique but the number and position of a plurality of such sequences is unique. This number and position of a plurality of sequences along a nucleic acid is analogous to a "barcode" that identifies the nucleic acid and its prokaryotic source. Nucleic acids can therefore be analyzed linearly, giving rise to a barcode that can be compared to known barcodes. Nucleic acids can alternatively be analyzed in their totality for the presence or absence of one or more probes bound thereto. In the latter instance, at least one probe is unique and thus specific for the nucleic acid of interest.

The method can be used to detect a plurality of different nucleic acids, and thus spores, in a sample.

Although the nucleic acid may be linearized or stretched prior to analysis, this is not necessary particularly if the detection system used is capable of analyzing both stretched and condensed nucleic acids. As used herein, stretching of the nucleic acid means that the nucleic acid is provided in a substantially linear, extended form rather than a compacted, coiled and/or folded form. Stretching the nucleic acid prior to analysis may be accomplished using an FFF device, various embodiments of the detection system, and the like. Thus, in one embodiment, the sample or mixture may be fractionated and stretched in the same FFF device (optionally in different chambers). These configurations are not required if the nucleic acid can be analyzed in a compacted form.

The target nucleic acids commonly have a phosphodiester backbone because this backbone is most common in vivo. Nucleic acid probes (i.e., probes that are nucleic acids themselves) are not so limited in their backbone composition and may include one or more modifications at their ends or internally (e.g., at an internucleotide linkage). Backbone modifications are known in the art and include but are not limited to phosphorothioate linkages, phosphodiester modified nucleic acids, combinations of phosphodiester and phosphorothioate nucleic acid, methylphosphonate, alkylphosphonates, phosphate esters, alkylphosphonothioates, phosphoramidates, carbamates, carbonates, phosphate triesters, acetamidates, carboxymethyl esters, methylphosphorothioate, phosphorodithioate, p-ethoxy, and combinations thereof. The nucleic acid probes may have a heterogeneous or homogeneous backbone.

The methods of the invention in part may be used to analyze nucleic acids using probes that recognize and specifically bind to particular nucleic acids. Binding of a probe to a nucleic acid may indicate the presence and location of a target site in the target nucleic acid, or it may simply indicate the presence of the nucleic acid, depending on user requirements. As used herein, a target nucleic acid that is bound by a probe is "labeled" with the probe and/or its detectable label.

As used herein, a probe is a molecule or compound that binds preferentially to the nucleic acid of interest (i.e., it has a greater affinity for the nucleic acid of interest than for other compounds). Its affinity for the nucleic acid of interest may be at least 2-fold, at least 5-fold, at least 10-fold, or more than its affinity for another compound. Probes with the greatest differential affinity are preferred in most embodiments.

The probes can be of any nature including but not limited to nucleic acid (including aptamers), peptide, carbohydrate, lipid, and the like. A nucleic acid probe such as an oligonucleotide can be used to recognize and bind nucleic acids such as DNA or RNA based on complementarity. The nucleic acid probe can be DNA, RNA, LNA, PNA, or some combination thereof, although it is not so limited. It can also comprise other nucleic acid mimics. Other probes for nucleic acid targets include but are not limited to sequence-specific major and minor groove binders and intercalators, nucleic acid binding peptides or proteins, etc.

As used herein a "peptide" is a polymer of amino acids connected preferably but not solely with peptide bonds. The probe may be an antibody or an antibody fragment. Antibodies include IgG, IgA, IgM, IgE, IgD as well as antibody variants such as single chain antibodies. Antibody fragments contain an antigen-binding site and thus include but are not limited to Fab and F(ab)$_2$ fragments.

The methods provided herein involve the use of probes that bind to the target nucleic acid in a sequence-specific manner. "Sequence-specific" when used in the context of a nucleic acid means that the probe recognizes a particular linear (or in some instances quasi-linear) arrangement of nucleotides. In some embodiments, the probes are "nucleic acid-specific" meaning that they bind specifically to a particular nucleic acid, possibly by virtue of a particular sequence or structure unique to that nucleic acid.

In some instances, nucleic acid probes will form at least a Watson-Crick bond with a target nucleic acid. In other instances, the nucleic acid probe can form a Hoogsteen bond with the target nucleic acid, thereby forming a triplex. Examples of these latter probes include molecules that recognize and bind to the minor and major grooves of nucleic acids (e.g., some forms of antibiotics). In some embodiments, the nucleic acid probes can form both Watson-Crick and Hoogsteen bonds with the nucleic acid. BisPNA probes, for instance, are capable of both Watson-Crick and Hoogsteen binding to a nucleic acid.

The nucleic acid probes of the invention can be any length ranging from at least 4 nucleotides to in excess of 1000 nucleotides. In preferred embodiments, the probes are 5-100 nucleotides in length, more preferably between 5-25 nucleotides in length, and even more preferably 5-12 nucleotides in length. The length of the probe can be any length of nucleotides between and including the ranges listed herein, as if each and every length was explicitly recited herein. For example, the length may be at least 5 nucleotides, at least 10 nucleotides, at least 15 nucleotides, at least 20 nucleotides, or at least 25 nucleotides, or more, in length. The length may range from at least 4, at least 5, at least 6, at least 7, at least 8, at least 9, at least 10, at least 12, at least 15, at least 20, at least 25, at least 50, at least 75, at least 100, at least 150, at least 200, at least 250, at least 500, or more nucleotides (including every integer therebetween as if explicitly recited herein). The length of probe can also determine the specificity of binding. Longer probes are desirable when unique sequences are being detected.

The probes are preferably single-stranded, but they are not so limited. For example, when the probe is a bisPNA it can adopt a secondary structure with the nucleic acid resulting in a triple helix conformation, with one region of the bisPNA clamp forming Hoogsteen bonds with the backbone of the nucleic acid and another region forming Watson-Crick bonds with the bases of the nucleic acid.

The nucleic acid probe hybridizes to a complementary sequence within the nucleic acid. The specificity of binding can be manipulated based on the hybridization conditions. For example, salt concentration and temperature can be modulated in order to vary the range of sequences recognized by the nucleic acid probes. Those of ordinary skill in the art will be able to determine optimum conditions for a desired specificity.

In some embodiments, the probes may be molecular beacons. When not bound to their targets, the molecular beacon probes form a hairpin structure and do not emit fluorescence since one end of the molecular beacon is a quencher molecule. However, when bound to their targets, the fluorescent and quenching ends of the probe are sufficiently separated so that the fluorescent end emits its characteristic wavelength.

The probes may be or may contain nucleic acid derivatives. As used herein, a "nucleic acid derivative" is a nucleic acid that contains non-naturally occurring elements. Nucleic acid derivatives may contain non-naturally occurring nucleotides and non-naturally occurring backbone linkages. These include substituted purines and pyrimidines such as C-5 propyne modified bases, 5-methylcytosine, 2-aminopurine, 2-amino-6-chloropurine, 2,6-diaminopurine, hypoxanthine, 2-thiouracil and pseudoisocytosine. Other such modifications are well known to those of skill in the art.

The nucleic acid derivatives may also encompass substitutions or modifications, such as in the bases and/or sugars. For example, they include nucleic acids having backbone sugars which are covalently attached to low molecular weight organic groups other than a hydroxyl group at the 3' position and other than a phosphate group at the 5' position. Thus, modified nucleic acids may include a 2'-O-alkylated ribose group. In addition, modified nucleic acids may include sugars such as arabinose instead of ribose.

In some embodiments, the probe is a peptide nucleic acid (PNA), a bisPNA clamp, a pseudocomplementary PNA (pcPNA), a locked nucleic acid (LNA), DNA, RNA such as siRNA, miRNA or RNAi, or a co-polymer that of such as DNA-LNA co-polymers. The probe can be a two-armed PNA (as described in co-pending U.S. patent application having Ser. No. 10/421,644 and publication number US 2003-0215864 A1 and published Nov. 20, 2003, and PCT application having serial number PCT/US03/12480 and publication number WO 03/091455 A1 and published Nov. 6, 2003, filed on Apr. 23, 2003).

PNAs are DNA analogs having their phosphate backbone replaced with 2-aminoethyl glycine residues linked to nucleotide bases through glycine amino nitrogen and methylenecarbonyl linkers. The backbone constituents of PNAs may be peptide linkages, or alternatively they may be non-peptide linkages. Examples include acetyl caps, amino spacers such as 8-amino-3,6-dioxaoctanoic acid (referred to herein as O-linkers), amino acids such as lysine (particularly useful if positive charges are desired in the PNA), and the like. Various PNA modifications are known and probes incorporating such modifications are commercially available from sources such as Boston Probes, Inc. PNAs are synthesized from monomers connected by a peptide bond (Nielsen, P. E. et al. *Peptide Nucleic Acids Protocols and Applications*, Norfolk: Horizon Scientific Press, p. 1-19 (1999)). They can be built with standard solid phase peptide synthesis technology.

Locked nucleic acid (LNA) is a modified RNA nucleotide. Synthesis and hybridization profiles are described by Braasch and Corey (Chem Biol. 2001 January; 8 (1):1-7. Review). Commercial nucleic acid synthesizers and standard phosphoramidite chemistry may be used to make LNA.

The probes can be synthesized in a manner that incorporates a detectable label directly into the growing nucleic acid. It is possible to synthesize nucleic acids de novo (e.g., using automated nucleic acid synthesizers) using detectably labeled nucleotides. Such nucleotides are commercially available from suppliers such as Amersham Pharmacia Biotech, Molecular Probes, and New England Nuclear/Perkin Elmer. The probes may be labeled with a detectable label. This can be accomplished by chemical means or by the introduction of active amino or thiol groups into nucleic acids. (Proudnikov and Mirabekov, Nucleic Acid Research, 24:4535-4532, 1996.) An extensive description of modification procedures that can be performed on a nucleic acid can be found in Hermanson, G. T., Bioconjugate Techniques, Academic Press, Inc., San Diego, 1996.

As used herein, "conjugated" means two entities stably bound to one another by any physiochemical means. It is important that the nature of the attachment is such that it does not substantially impair the effectiveness of either entity. Keeping these parameters in mind, any covalent or non-covalent linkage known to those of ordinary skill in the art may be employed. In some embodiments, covalent linkage is preferred. Non-covalent conjugation includes hydrophobic interactions, ionic interactions, high affinity interactions such as biotin-avidin and biotin-streptavidin complexation and other affinity interactions. The conjugations or modifications described herein employ routine chemistry, which is known to those skilled in the art of chemistry. The use of linkers such as mono- and hetero-bifunctional linkers is documented in the literature (e.g., Hermanson, 1996).

A detectable label is a moiety, the presence of which can be ascertained directly or indirectly. Generally, detection of the label involves the creation of a detectable signal such as for example an emission of energy. The label may be of a chemical, peptide or nucleic acid nature although it is not so limited. The nature of label used will depend on a variety of factors, including the nature of the analysis being conducted, the type of energy source and detector used, and the type of polymer and probe. The label should be sterically and chemically compatible with the constituents to which it is bound.

The label can be detected directly for example by its ability to emit and/or absorb electromagnetic radiation of a particular wavelength. A label can be detected indirectly for example by its ability to bind, recruit and, in some cases, cleave another moiety which itself may emit or absorb light of a particular wavelength (e.g., an epitope tag such as the FLAG epitope, an enzyme tag such as horseradish peroxidase, etc.).

The detectable label can be selected from the group consisting of directly detectable labels such as a fluorescent molecule (e.g., fluorescein, rhodamine, tetramethylrhodamine, R-phycoerythrin, Cy-3, Cy-5, Cy-7, Texas Red, Phar-Red, allophycocyanin (APC), fluorescein amine, eosin, dansyl, umbelliferone, 5-carboxyfluorescein (FAM), 2'7'-dimethoxy-4'5'-dichloro-6-carboxyfluorescein (JOE), 6 carboxyrhodamine (R6G), N,N,N',N'-tetramethyl-6-carboxyrhodamine (TAMRA), 6-carboxy-X-rhodamine (ROX), 4-(4'-dimethylaminophenylazo) benzoic acid (DABCYL), 5-(2'-aminoethyl) aminonaphthalene-1-sulfonic acid (EDANS), 4-acetamido-4'-isothiocyanatostilbene-2,2'disulfonic acid, acridine, acridine isothiocyanate, r-amino-N-(3-vinylsulfonyl)phenylnaphthalimide-3,5, disulfonate (Lucifer Yellow VS), N-(4-anilino-1-naphthyl)maleimide, anthranilamide, Brilliant Yellow, coumarin, 7-amino-4-methylcoumarin, 7-amino-4-trifluoromethylcouluarin (Coumarin 151), cyanosine, 4', 6-diaminidino-2-phenylindole (DAPI), 5',5"-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin diethylenetriamine pentaacetate, 4,4'-diisothiocyanatodihydro-stilbene-2,2'-disulfonic acid, 4,4'-diisothiocyanatostilbene-2,2'-disulfonic acid, 4-dimethylaminophenylazophenyl-4'-isothiocyanate (DABITC), eosin isothiocyanate, erythrosin B, erythrosin isothiocyanate, ethidium, 5-(4,6-dichlorotriazin-2-yl) aminofluorescein (DTAF), QFITC (XRITC), fluorescamine, IR144, IR1446, Malachite Green isothiocyanate, 4-methylumbelliferone, ortho cresolphthalein, nitrotyrosine, pararosaniline, Phenol Red, B-phycoerythrin, o-phthaldialdehyde, pyrene, pyrene butyrate, succinimidyl 1-pyrene butyrate, Reactive Red 4 (Cibacron® Brilliant Red 3B-A), lissamine rhodamine B sulfonyl chloride, rhodamine B, rhodamine 123, rhodamine X, sulforhodamine B, sulforhodamine 101, sulfonyl chloride derivative of sulforhodamine 101, tetramethyl rhodamine, riboflavin, rosolic acid, and terbium chelate derivatives), a chemiluminescent molecule, a bioluminescent molecule, a chromogenic molecule, a radioisotope (e.g., $P^{32}$ or $H^3$, $^{14}C$, $^{125}I$ and $^{131}I$), an electron spin resonance molecule (such as for example nitroxyl radicals), an optical or electron density molecule, an electrical charge transducing or transferring molecule, an electromagnetic molecule such as a magnetic or paramagnetic bead or particle, a semiconductor nanocrystal or nanoparticle (such as quantum dots described for example in U.S. Pat. No. 6,207,392 and commercially available from Quantum Dot Corporation and Evident Technologies), a colloidal metal, a colloid gold nanocrystal, a nuclear magnetic resonance molecule, and the like.

The detectable label can also be selected from the group consisting of indirectly detectable labels such as an enzyme (e.g., alkaline phosphatase, horseradish peroxidase, β-galactosidase, glucoamylase, lysozyme, luciferases such as firefly luciferase and bacterial luciferase (U.S. Pat. No. 4,737,456); saccharide oxidases such as glucose oxidase, galactose oxidase, and glucose-6-phosphate dehydrogenase; heterocyclic oxidases such as uricase and xanthine oxidase coupled to an enzyme that uses hydrogen peroxide to oxidize a dye precursor such as HRP, lactoperoxidase, or microperoxidase), an enzyme substrate, an affinity molecule, a ligand, a receptor, a biotin molecule, an avidin molecule, a streptavidin molecule, an antigen (e.g., epitope tags such as the FLAG or HA epitope), a hapten (e.g., biotin, pyridoxal, digoxigenin fluorescein and dinitrophenol), an antibody, an antibody fragment, a microbead, and the like. Antibody fragments include Fab, F(ab)$_2$, Fd and antibody fragments which include a CDR3 region.

In some embodiments where two or more probes must bind to a nucleic acid for identification or analysis, the detectable label may be a member of a FRET fluorophore pair. FRET fluorophore pairs are two fluorophores that are capable of undergoing FRET to produce and simultaneously reduce (or eliminate) a detectable signal when positioned in proximity to one another. Examples of donors include Alexa 488, Alexa 546, BODIPY 493, Oyster 556, Fluor (FAM), Cy3 and TMR (Tamra). Examples of acceptors include Cy5, Alexa 594, Alexa 647 and Oyster 656. Cy5 can work as a donor with Cy3, TMR or Alexa 546, as an example. FRET should be possible with any fluorophore pair having fluorescence maxima spaced at 50-100 nm from each other.

The nucleic acid may be labeled in a sequence non-specific manner. For example, the DNA backbone may be labeled with a backbone stain. Examples of backbone stains include intercalating dyes such as phenanthridines and acridines (e.g., ethidium bromide, propidium iodide, hexidium iodide, dihydroethidium, ethidium homodimer-1 and -2, ethidium monoazide, and ACMA); minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc.

Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

The nucleic acid be analyzed using a single molecule analysis system. A single molecule detection system is an integrated device capable of analyzing single molecules individually (i.e., separately from other molecules). Such a system may be capable of analyzing single molecules in a linear manner and/or in their totality. In certain embodiments in which detection is based predominately on the presence or absence of a sequence, label and/or signal, linear analysis may not be required. However, there are other embodiments embraced by the invention which would benefit from the ability to analyze linearly molecules (preferably nucleic acids) in a sample. These include applications in which the sequence of the nucleic acid is desired, or in which the polymers are distinguished based on a spatial labeling pattern rather than the binding of one or more unique probes. A single molecule analysis system need not rely on signal from a plurality of molecules.

The nucleic acids can be analyzed using linear polymer analysis systems. A linear polymer analysis system is an integrated device that analyzes polymers such as nucleic acids, in a linear manner (i.e., starting at one location on the polymer and then proceeding linearly in either direction therefrom). As a nucleic acid is analyzed, the detectable labels attached thereto are detected in either a sequential or simultaneous manner. When detected simultaneously, the signals usually form an image of the polymer, from which distances between labels can be determined. When detected sequentially, the signals are viewed in a signal intensity vs. time histogram that can then be translated into a map, with knowledge of the velocity of the nucleic acid through the device. It is to be understood that in some embodiments, the nucleic acid is attached to a solid support, while in others it is free flowing. In either case, the velocity of the nucleic acid as it moves past, for example, an energy source or a detector, will aid in determining the position of the probes relative to each other and relative to other detectable markers that may be present on the nucleic acid.

An example of a single molecule analysis system that is a linear polymer analysis system is the GeneEngine™ (U.S. Genomics, Inc., Woburn, Mass.). The Gene Engine™ system is described in PCT patent applications WO98/35012 and WO00/09757, published on Aug. 13, 1998, and Feb. 24, 2000, respectively, and in issued U.S. Pat. No. 6,355,420 B1, issued Mar. 12, 2002. It allows single nucleic acids to be passed in a linear manner through an interaction station in which the nucleotides of the nucleic acid target and/or the nucleic acid probe are directly and optionally individually exposed to an energy or excitation source. The energy source may be a laser having a set wavelength. The mechanism for signal emission and detection will depend on the type of label sought to be detected, as described herein. An example of a single molecule analysis system is the Trilogy™ (U.S. Genomics, Inc., Woburn, Mass.), which can analyze molecules in compacted or unstretched form.

The systems described herein will encompass at least one detection system. The nature of such detection systems will depend upon the nature of the detectable label. The detection system can be selected from any number of detection systems known in the art. These include an electron spin resonance (ESR) detection system, a charge coupled device (CCD) detection system, a fluorescent detection system, an electrical detection system, a photographic film detection system, a chemiluminescent detection system, an enzyme detection system, an atomic force microscopy (AFM) detection system, a scanning tunneling microscopy (STM) detection system, an optical detection system, a nuclear magnetic resonance (NMR) detection system, a near field detection system, and a total internal reflection (TIR) detection system, many of which are electromagnetic detection systems.

Other single nucleic acid analytical methods can also be used to analyze the nucleic acid. These include fiber-fluorescence in situ hybridization (fiber-FISH) (Bensimon, A. et al., *Science* 265 (5181):2096-2098 (1997)). In fiber-FISH, nucleic acids are elongated and fixed on a surface by molecular combing. Hybridization with fluorescently labeled probe sequences allows determination of sequence landmarks on the nucleic acids. The method requires fixation of elongated nucleic acids so that molecular lengths and/or distances between markers can be measured. Pulse field gel electrophoresis can also be used to analyze the labeled nucleic acids. Pulse field gel electrophoresis is described by Schwartz, D. C. et al., *Cell* 37 (1):67-75 (1984). Other nucleic acid analysis methods are described by Otobe, K. et al., *Nucleic Acids Res.* 29 (22):E109 (2001), Bensimon, A. et al. in U.S. Pat. No. 6,248,537, issued Jun. 19, 2001, Herrick, J. et al., *Chromosome Res.* 7 (6):409:423 (1999), Schwartz in U.S. Pat. No. 6,150,089 issued Nov. 21, 2000 and U.S. Pat. No. 6,294,136, issued Sep. 25, 2001. Other linear polymer analysis methods can also be used, and the invention is not intended to be limited to solely those listed herein.

The present invention is further illustrated by the following Examples, which in no way should be construed as further limiting.

EXAMPLES

Example 1

Method for Isolating HMW Genomic DNA from Prokaryotic Spores $10^8$ spores were resuspended in 100 µl spore decoating solution (8M urea, 1% SDS, 50 mM Tris, 10 mM EDTA, 2% β-mercaptoethanol, pH 10). The spores were incubated at 90° C. for 5 minutes, spun down and resuspended in 1 ml wash solution (5 mM Tris, 5 mM EDTA, 0.05% Tween 20, 0.05% Triton-X-100, pH 8). The spores were washed three times, gently pelleted and then resuspended in 100 µl of a first lysing buffer (10× wash solution, pH 8). Lysozyme was added to a final concentration of 2 mg/ml. PlyG lysin can be used at a final concentration of 10 U/ml, for example, for *B. anthracis* spores. The mixture was incubated in a 37° C. water bath for 60 minutes, or until spores were phase dark in a phase contrast microscope, with minimal agitation. The mixture was then spun, the supernatant was removed, and the pellets were resuspended in a second lysis solution (6 M urea, 2% β-mercaptoethanol (or DTT), 1% N-lauryl sarcosine, 10 mM EDTA, 50 mM Tris, pH 7.4). To digest proteins and break down crosslinks, proteinase K was added to a final concentration of 1 mg/ml. The sample was incubated in a 55° C. water bath for 30 minutes or until lysate was clear. In order to remove contaminants from the sample, the lysate was placed in dialysis membrane (500,000 kDa cut-off SpectraPor PVDF membrane tubing from Spectrum Labs) and dialyzed against 2 liters of 1:100 diluted lysis solution for 16 hours. The buffer was then changed to 1×TE buffer and the sample was dialyzed for an additional 16 hours.

Figure 1:
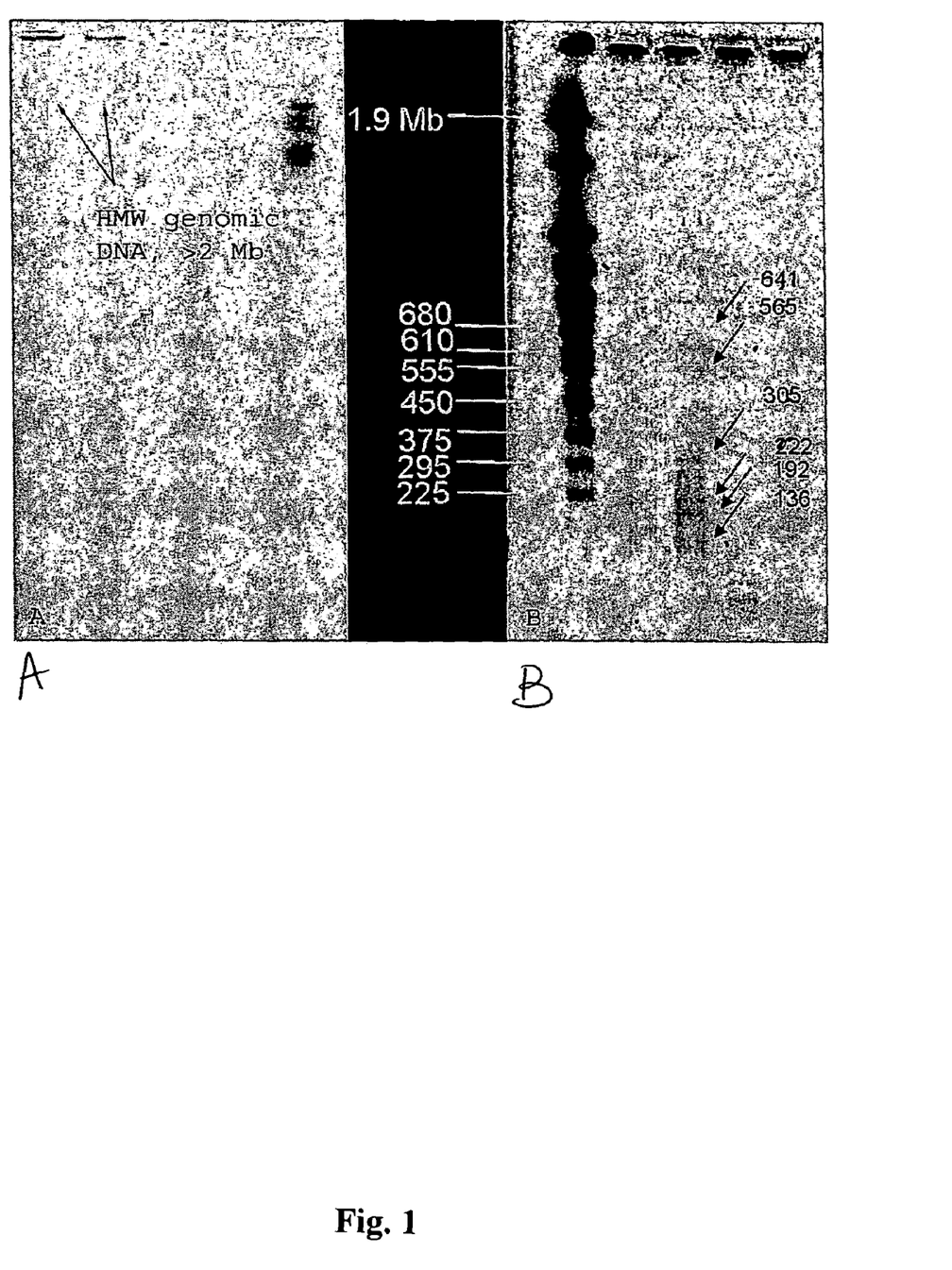
FIG. 1A depicts a pulsed field agarose gel showing HMW DNA isolated according to the invention from *B. anthracis* spores in lanes 1 and 2. Yeast chromosome markers of 1900, 1640, 1120, 1100, 945, 915, 815, 785, 745, 680, 610, 555, 450, 375, 295 and 225 kilobases are shown in lane 5.
FIG. 1B depicts a pulsed field agarose gel showing *B. anthracis* genomic DNA isolated according to the invention and digested with NotI and PmeI in lanes 3 and 4, respectively. Yeast chromosome markers of 1900, 1640, 1120, 1100, 945, 915, 815, 785, 745, 680, 610, 555, 450, 375, 295 and 225 kilobases are shown in lane 1.
Figure 2:
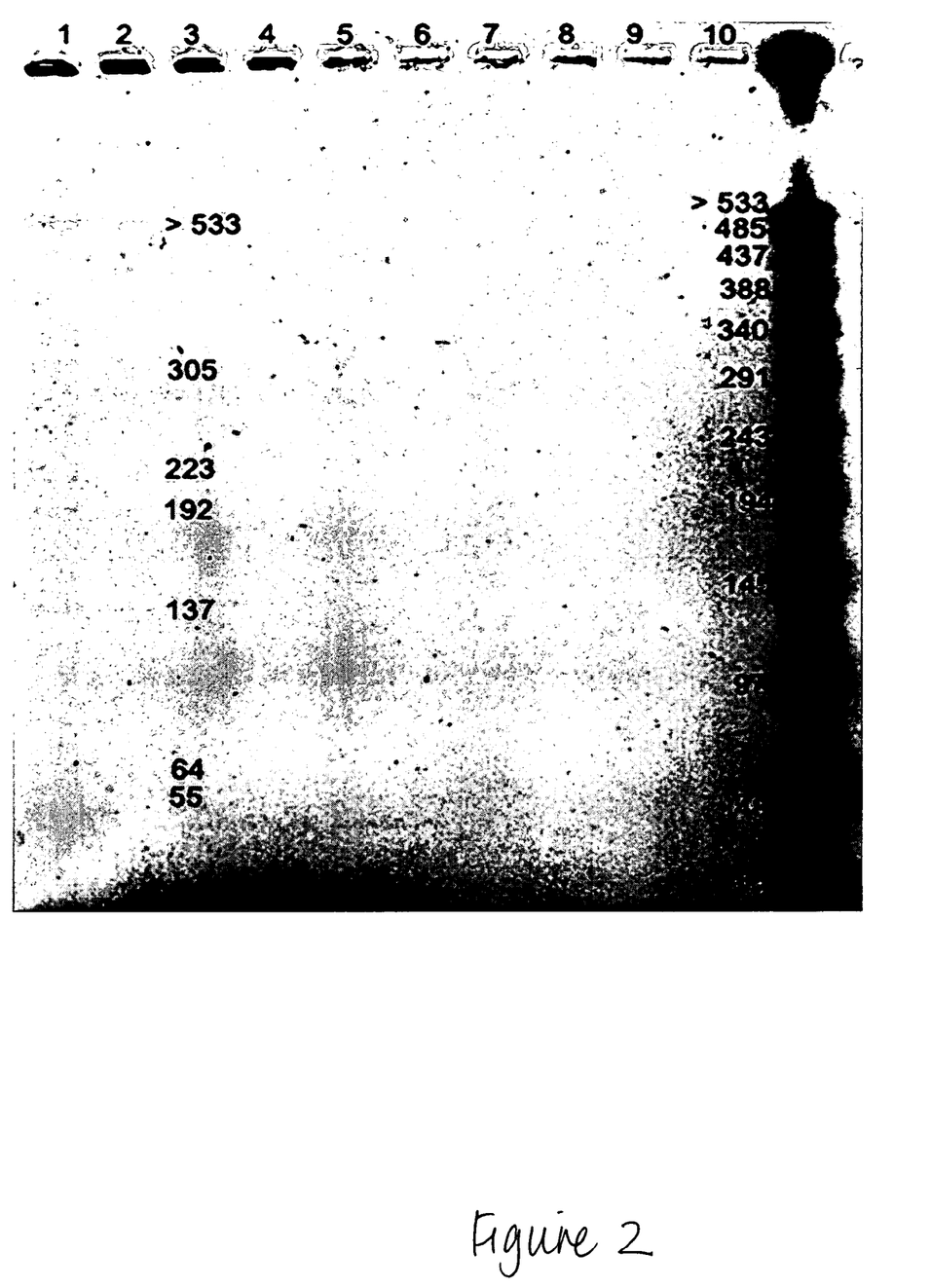
FIG. 2 depicts a pulsed field agarose gel showing *B. anthracis* (strain NNR-1) genomic DNA digested with Not I in lanes 1 and 2. DNA size markers in kilobases are shown in lane 11.

FIGS. 1 and 2 illustrate the nucleic acids harvested using this technique. Nucleic acids on the order to 1 Mb have been observed using this method. $10^8$ initial spores routinely yield on the order of 1 µg of DNA. The methods yield both plasmid and chromosomal DNA, as well as RNA.

REFERENCES

1. Santo, L. Y. and R. H. Doi. Ultrastructural Analysis During Germinatin and Outgrowth of *Bacillus subtilis* Spores. *J Bacteriol.*, 1974; 120 (1):475-481.
2. Driks, A. and P. Setlow. Morphogenesis and properties of the bacterial spore. In Prokaryotic development, ASM Press, 2000; Editors Y. V. Brun and L. J. Shimkets. 191-218.
3. La Duc, M. T., M. Satomi and K. Venkateswaran. *Bacillus odysseyi* sp. Nov., a round-spore-forming bacillus isolated from the Mars Odyssey spacecraft. *Int J Syst Evol Microbiol*, 2004; 54: 195-201.
4. Cano, R. J. and M. K. Borucki. Revival and identification of bacterial spores in 25-40-million year old Dominican amber. *Science*, 1995; 268:1060-64.
5. Kornberg, A., J. A. Spudich, D. L. Nelson and M. Deutscher. Origin of proteins in sporulation. *Annu. Rev. Biochem.* 1968; 37:51-78.
6. Goldman, R. C., and D. J. Tipper. *Bacillus subtilis* spore coats; complexity and purification of a unique polypeptide component. *J. Bacteriol.* 1978; 135:1091-1106.
7. Pandey, N. K. and A. I. Aronson. Properties of the *Bacillus subtilis* spore coat. *J. Bacteriol.* 1979; 137:1208-1218.
8. Jenkinson, H. F., W. D. Sawyer and J. Mandelstam. Synthesis and order of assembly of spore coat proteins in *Bacillus subtilis*. *J. Gen. Microbiol.* 1981; 123:1-16.
9. Warth, A. D. and J. L. Strominger. Structure of the peptidoglycan of bacterial spores: occurrence of the lactam of muramic acid. *Proc. Natl. Acad. Sci. USA*. 1969; 64:528-535.
10. Warth, A. D. and J. L. Strominger. Structure of the peptidoglycan from vegetative cell walls of *Bacillus subtilis*. *Biochemistry*. 1971; 10:4349-4358.
11. Warth, A. D. and J. L. Strominger. Structure of the peptidoglycan from spores of *Bacillus subtilis*. *Biochemistry*. 1972; 11:1389-1396.
12. Arith, A., P. Zollner, G. Allmaier and S. F. Foster. Structural analysis of *Bacillus subtilis* 168 endospore peptidoglycan and its role during differentiation. *J. Bacteriol.* 1996; 178:6173-6183.
13. Popham, D. L., J. Helin, C. E. Costello and P. Setlow. Analysis of the peptidoglycan structure of *Bacillus subtilis* endospores. *J. Bacteriol.* 1996; 178:6451-6458.
14. Nicholson, W. L. and P. Setlow. Dramatic increase in the negative superhelicity of plasmid DNA in the forespore compartment of sporulating cells of *Bacillus subtilis*. *J. Bacteriol.* 1990; 172:7-14.

15. Pogliano, K., E. Harry and R. Losick. Visualization of the subcellular location of sporulation proteins in *Bacillus subtilis* using immunofluorescence microscopy. *Mol. Microbiol.* 1995; 18:459-470.
16. Griffith, J., A. Makhov, L. Santiago-Lara and P. Setlow. Electron microscopic studies of the interaction between a *Bacillus* α/β-type small, acid-soluble s pore protein with DNA: protein binding is cooperative, stiffens the DNA and induces negative supercoiling. *Proc. Natl. Acad. Sci.* USA. 1994; 91:8224-8228.
17. Mohr, S. C., N. V. H. A. Sokolov, C. He and P. Setlow. Binding of small acid-soluble spore proteins from *Bacillus subtilis* changes the conformation of DNA from B to A. *Proc. Natl. Acad. Sci.* USA. 1991; 88:77-81.
18. Setlow, P. DNA in dormant spores of *Bacillus* species is in an A-like conformation. *Mol. Microbiol.* 1992; 6:563-567.
19. Nicholson, W. L., B. Setlow and P. Setlow. Binding of DNA in vitro by a small, acid-soluble spore protein and its effect on DNA topology. *J. Bacteriol.* 1990; 172:6900-6906.
20. Fairhead, H. and P. Setlow. Binding of DNA to α/β-type small, acid-soluble proteins from spores of *Bacillus* or *Clostridium* species prevents formation of cytosine-thymine dimers and dipyrimidine photoadducts upon ultraviolet irradiation. *J. Bacteriol.* 1992; 174:2874-2880.
21. Ivnitski D., D. J. O'Neil, A. Gattuso, R. Schlicht, M. Calidonna and R. Fisher. Nucleic acid approaches for detection and identification of biological warfare and infectious disease agents. *Biotechniques.* 2003; 35:862-869.

EQUIVALENTS

It should be understood that the preceding is merely a detailed description of certain embodiments. It therefore should be apparent to those of ordinary skill in the art that various modifications and equivalents can be made without departing from the spirit and scope of the invention, and with no more than routine experimentation.

All references, patents and patent applications referred to herein are incorporated by reference herein in their entirety.

What is claimed is:

1. A method for harvesting high molecular weight nucleic acids from bacterial spores comprising
   degrading spore coats of bacterial spores using a detergent and a reducing agent in a basic solution, thereby producing decoated spores,
   lysing spore cell walls of the decoated spores using a solution comprising lysozyme and a chelator,
   degrading proteins of the decoated spores using a solution comprising a protease and a mild detergent, and harvesting high molecular weight nucleic acids that are at least 30 kilobases in size.
2. The method of claim 1, wherein the high molecular weight nucleic acids that are at least 30 kilobases in size are at least 250 kilobases in size.
3. The method of claim 1, wherein the bacterial spores are *Bacillus* spores.
4. The method of claim 3, wherein the *Bacillus* spores are *B. anthracis* spores.
5. The method of claim 1, wherein the bacterial spores are *Clostridium* spores.
6. The method of claim 1, wherein the bacterial spores are non-germinating.
7. A method for harvesting nucleic acids from bacterial spores comprising
   contacting bacterial spores with a decoating solution for a time that is from about 5 minutes to less than 45 minutes at a temperature greater than 75° C. to degrade spore coats of the bacterial spores, thereby producing decoated spores,
   sequentially contacting decoated spores with a first lysing solution comprising lysozyme and a second lysing solution comprising a protease for sufficient times under conditions sufficient to degrade spore cell walls and proteins of the decoated spores, and
   harvesting nucleic acids that are at least 30 kilobases in size.
8. The method of claim 7, wherein the nucleic acids that are at least 30 kilobases in size are at least 250 kilobases in size.
9. The method of claim 7, wherein the bacterial spores are *Bacillus* spores.
10. The method of claim 9, wherein the *Bacillus* spores are *B. anthracis* spores.
11. The method of claim 7, wherein the bacterial spores are *Clostridium* spores.
12. The method of claim 7, wherein the bacterial spores are non-germinating.

* * * * *